(12) United States Patent
Müllertz et al.

(10) Patent No.: US 6,264,946 B1
(45) Date of Patent: Jul. 24, 2001

(54) ANIMAL FEED ADDITIVES

(75) Inventors: Anette Müllertz, Charlottenlund; Lene Beck Jensen, Copenhagen; Betina Kastbjerg Jensen, København, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/169,588

(22) Filed: Oct. 9, 1998

Related U.S. Application Data

(63) Continuation of application No. PCT/DK97/00172, filed on Apr. 17, 1997.

(30) Foreign Application Priority Data

Apr. 23, 1996 (DK) .................................................. 0478/96

(51) Int. Cl.[7] .................................................. A61K 38/54
(52) U.S. Cl. ..................... 424/94.2; 424/94.61; 435/200; 435/209
(58) Field of Search ............................... 424/94.2, 94.61; 435/200, 209

(56) References Cited

FOREIGN PATENT DOCUMENTS

| WO 92/03541 | 3/1992 | (WO) . |
| WO 94/21785 | 9/1994 | (WO) . |
| 9523514 * | 9/1995 | (WO) . |
| WO 96/05739 | 2/1996 | (WO) . |
| WO 96/23062 | 8/1996 | (WO) . |

OTHER PUBLICATIONS

He et al. (1994) Enzyme Microb Technol 16:696–702.

He et al., (1993) Enzyme Microb. Technol. 15:13–18.

* cited by examiner

*Primary Examiner*—Jean C. Witz
(74) *Attorney, Agent, or Firm*—Elias J. Lambiris, E

(57) ABSTRACT

The present invention relates to the combined use, simultaneous or sequential, of one or more xylanolytic enzymes of Type I with one or more xylanolytic enzymes of Type II in animal feed. It also relates to animal feed and animal feed additives comprising such combination of xylanolytic enzymes.

24 Claims, 4 Drawing Sheets

ANIMAL FEED ADDITIVES

CROSS-REFERENCE TO RELATED APPLICATIONS

This application is a continuation of PCT/DK97/00172 filed Apr. 17, 1997 which claims priority under 35 U.S.C. 119 of Danish application 0478196 filed Apr. 23, 1996, the contents of which are fully incorporated herein by reference.

TECHNICAL FIELD

The present invention relates to the combined use in animal feed of one or more xylanolytic enzymes of Type I with one or more xylanolytic enzymes of Type II, as defined herein. It also relates to animal feed and animal feed additives comprising such combination of xylanolytic enzymes.

BACKGROUND ART

The types and amount of plant raw materials which can be used as components in animal feed will often be limited by the ability of the animals to digest them. Feed enhancing enzymes are enzymes, usually of microbial origin, that by improving feed digestibility are able to increase the efficiency of its utilization.

When added to animal feed, feed enhancing enzymes improve the in vivo breakdown of plant cell wall material partly due to a reduction of the intestinal viscosity, whereby a better utilization of the plant nutrients by the animal is achieved. In this way the growth rate and/or feed conversion ratio (i.e. the weight of ingested feed relative to weight gain) of the animal becomes improved.

Xylanolytic enzymes (EC 3.2.1.8) are well known as feed enhancing enzymes. According to one theory, their primary effect is to reduce the viscosity of the feed, whereas another theory focuses on the xylanases increasing the availability of nutrients embedded in the plant cell wall. Thus WO 94/21785 describes xylanases derived from *Aspergillus aculeatus* and their use as animal feed additives, in particular in animal feed compositions containing high amounts of arabinoxylans and glucuronoxylans, e.g. feed containing cereals such as barley, wheat, rye or oats or maize.

WO 95/23514 describes a process for reducing the viscosity of a plant material and for separating plant material into desirable components, which process comprises treating the plant material with a xylanase preparation having a specific activity on water-soluble/water in-soluble pentosans. However, WO 95/23514 does not relate to mixtures of xylanases.

SUMMARY OF THE INVENTION

According to the present invention it has now been found that xylanolytic enzymes can be distinguished by the way they degrade different substrates. Moreover it has surprisingly been found that the combined action of two different types of xylanolytic enzymes is improved as compared to the action of the two separate enzymes, i.e. a synergistic effect occurs.

Therefore, one main object of the invention is the combined use of these two types of xylanolytic enzymes in animal feed. In particular, they are used simultaneously and/or sequentially.

It is another main object of the present invention to provide an animal feed additive which increases energy uptake from animal feed. Accordingly, in one main aspect, the present invention provides an animal feed additive which comprises a mixture of one or more xylanolytic enzymes of Type I with one or more xylanolytic enzymes of Type II, Type I and Type II as defined herein.

BRIEF DESCRIPTION OF THE DRAWINGS

The present invention is further illustrated by reference to the accompanying drawing, in which.

DETAILED DISCLOSURE OF THE INVENTION

Figure 1:
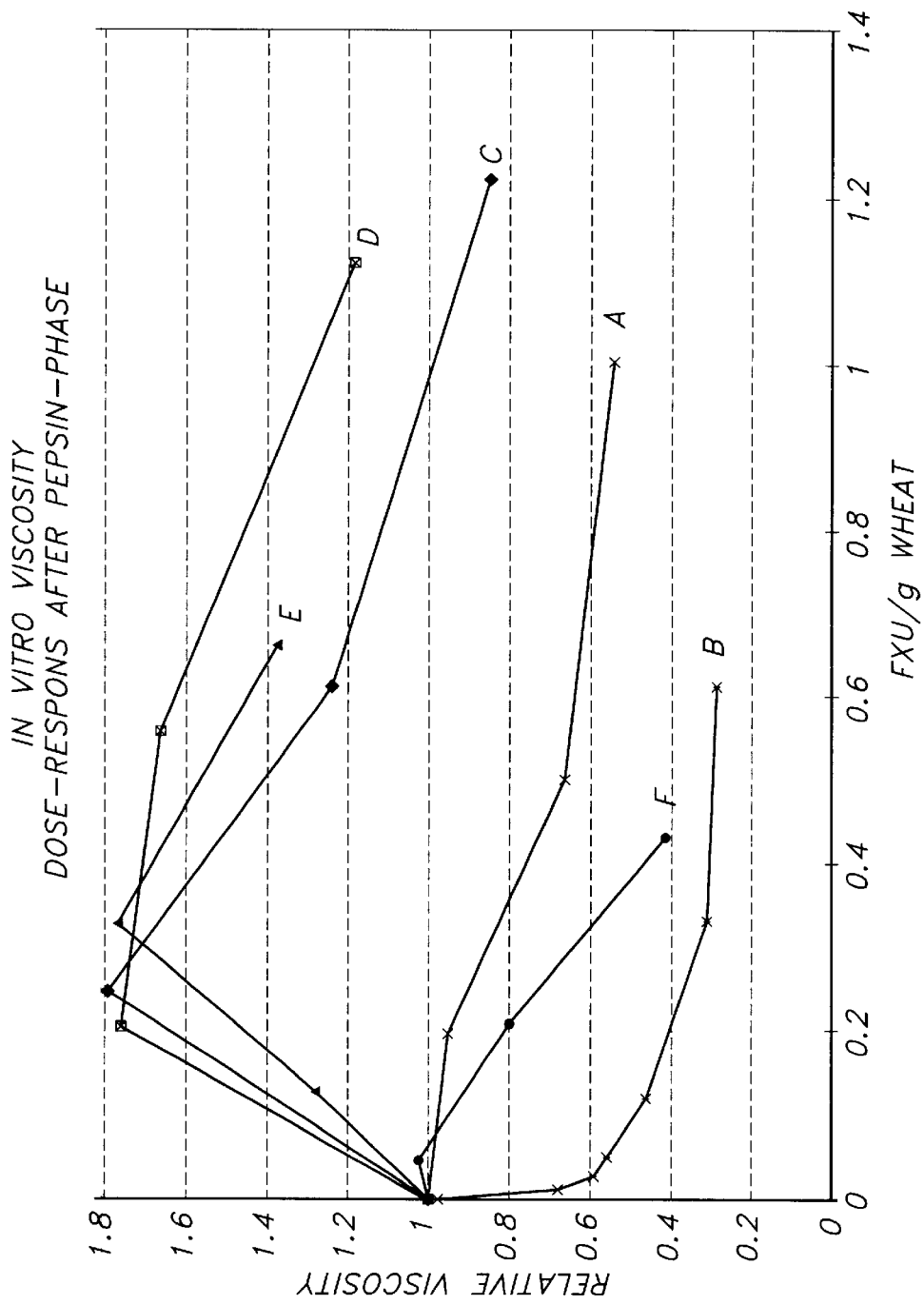
FIG. 1 shows the action of six different xylanolytic enzymes [viz. a multicomponent *Trichoderma reesei* xylanase preparation (A); a monocomponent *Aspergillus aculeatus* xylanase preparation (B); a monocomponent *Humicola insolens* xylanase preparation (C); a monocomponent *Thermomyces lanuginosus* xylanase preparation (D); a multicomponent *Humicola insolens* xylanase preparation (E) and a multicomponent *Trichoderma xylanase* preparation (F)] on the viscosity of a wheat suspension determined after the so-called pepsin phase according to Example 1, presented as relative viscosity (%) versus enzyme concentration (FXU/g wheat)

All patents, patent applications, and literature references referred to herein are hereby incorporated by reference in their entirety.

Xylanolytic Enzymes of Type I and Type II

According to the present invention it has now been found that xylanolytic enzymes can be distinguished by the way they degrade different substrates. Moreover it has surprisingly been found that the combined action of two different types of xylanolytic enzymes is increased as compared to the action of the two separate enzymes, i.e. a synergistic effect occurs.

The type of a xylanolytic enzyme may e.g. be determined by reference to its action on the viscosity of a wheat suspension. As defined herein, xylanolytic enzymes of Type I increase initial viscosity of a wheat suspension, whereas the initial viscosity of a wheat suspension is unaffected or becomes decreased by the action of a xylanolytic enzyme of Type II. In particular, the increased initial viscosity referred to above refers to FIGS. 1 and 2 hereof, which show an initially or at low FXU-doses increased relative viscosity.

The combined action of the two different types of xylanolytic enzymes referred to above can be simultaneous, i.e.

the two enzymes are active at the same time, or sequential, i.e. one type is acting first, the second type subsequently. In the sequential type of action the first type may be active or non-active, when the second type excerts its effect, viz. a simultaneous and sequential, and a pure sequential action, respectively. In all these cases a synergistic effect is observed on the viscosity of the feed.

An assay for determining the type of xylanolytic enzyme is described in more detail in Example 1.

Animal Feed and Animal Feed Additives

The present invention provides an animal feed as well as an animal feed additive, which comprises a mixture of one or more xylanolytic enzymes of Type I with one or more xylanolytic enzymes of Type II.

In the context of this invention, in particular, an animal feed means any natural or artificial diet, meal or the like or components of such meals intended or suitable for being eaten, taken in, or digested by an animal.

In the context of this invention, an animal feed additive is an enzyme preparation comprising one or more feed enhancing enzyme(s) and suitable carriers and/or excipients. In particular, the enzyme preparation is provided in a form that is suitable for being added to animal feed. The animal feed additive of the invention may be prepared in accordance with methods known in the art and may be provided in the form of a dry preparation or a liquid preparation. The enzyme to be included in the preparation, may optionally be stabilized in accordance with methods known in the art.

The animal feed additive of the invention may be a granulated enzyme product which may readily be mixed with feed components, or more preferably, form a component of a pre-mix. The granulated enzyme product may be coated or uncoated. The particle size of the enzyme granulates preferably is compatible with that of feed and pre-mix components. This provides a safe and convenient mean of incorporating enzymes into feeds.

Also, the animal feed additive of the invention may be a stabilized liquid composition, which may be an aqueous or oil-based slurry.

The animal feed additive of the invention may exert its effect either in vitro or in vivo. The effect may be exerted by pre-treating an animal feed, if desired followed by an inactivation of the enzymes. But usually the xylanases exert their effect in vivo, i.e. they act directly in the digestive system of the animal, during the digestion. The feed additive of the invention is particularly suited for addition to animal feed compositions containing high amounts of arabinoxylans and glucuronoxylans, e.g. feed containing cereals such as wheat, barley, rye, oats, or maize.

In a preferred embodiment an animal feed additive is provided in which the ratio of xylanolytic enzymes of Type I to xylanolytic enzymes of Type II is in the range of from about 1/9 to about 9/1, determined in terms of xylanolytic activity, i.e. 10–90% of the total amount of xylanolytic activity, e.g. determined in terms of FXU, is ascribable to a xylanolytic enzyme of Type I.

In another preferred embodiment an animal feed additive is provided in which the ratio of xylanolytic enzymes of Type I to xylanolytic enzymes of Type II is in the range of from about 2/8 to about 8/2, determined in terms of xylanolytic activity, i.e. 20–80% of the total amount of xylanolytic activity, e.g. determined in terms of FXU, is ascribable to a xylanolytic enzyme of Type I.

In a third preferred embodiment an animal feed additive is provided in which the ratio of xylanolytic enzymes of Type I to xylanolytic enzymes of Type II is in the range of from about 3/7 to about 7/3, determined in terms of xylanolytic activity, i.e. 30–70% of the total amount of xylanolytic activity, e.g. determined in terms of FXU, is ascribable to a xylanolytic enzyme of Type I.

In a fourth preferred embodiment an animal feed additive is provided in which the ratio of xylanolytic enzymes of Type I to xylanolytic enzymes of Type II is in the range of from about 4/6 to about 6/4, determined in terms of xylanolytic activity, i.e. 40–60% of the total amount of xylanolytic activity, e.g. determined in terms of FXU, is ascribable to a xylanolytic enzyme of Type I.

In a fifth preferred embodiment an animal feed additive is provided in which the ratio of xylanolytic enzymes of Type I to xylanolytic enzymes of Type II is about 5/5, determined in terms of xylanolytic activity, i.e. xylanolytic enzymes of Type I and Type II is present in approximately equal activities, e.g. determined in terms of FXU.

In a sixth preferred embodiment an animal feed additive is provided in which the ratio of xylanolytic enzymes of Type I to xylanolytic enzymes of Type II is in the range of from about 1/20 to about 20/1, determined in terms of xylanolytic activity, i.e. 5–95% of the total amount of xylanolytic activity, e.g. determined in terms of FXU, is ascribable to a xylanolytic enzyme of Type I. The particular embodiment of 1/20 of type II/type I has turned up to be very satisfactory.

Other preferred ratios are 125:1, 100:1, 75:1, 50:1 and 25:1 (type I: type II or vice versa).

Monocomponent Preparations

In a preferred embodiment, the present invention provides an animal feed additive, in which one or more of the xylanolytic enzymes are provided in the form of a monocomponent preparation. In the context of this invention, a monocomponent preparation is an enzyme preparation, in which preparation essentially all of the xylanolytic activity (i.e. the xylanolytic activity detectable) is owing to a single xylanase component. The monocomponent preparation may preferably be obtained by way of recombinant DNA technology.

In a more specific embodiment all xylanolytic enzymes are provided in the form of monocomponent preparations.

Feed Enhancing Enzymes

In a further preferred embodiment, the feed additive of the invention comprises additional feed enhancing enzymes.

In the context of this invention feed enhancing enzymes comprise but are not limited to other xylanases, α-galactosidases, β-galactosidases, in particular lactases, phytases, β-glucanases, in particular endo-β-1,4-glucanases and endo-β-1,3(4)-glucanases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases and lipolytic enzymes such as lipases and cutinases.

Microbial Sources

The xylanolytic enzymes of Type I and Type II according to the invention may originate from any source of xylanolytic enzymes. Preferably the xylanolytic enzymes are originally derived from microbial sources, and may in particular be of fungal origin, of bacterial origin, or derived from a yeast strain. In case of recombinant xylanolytic enzymes, any host cell can be employed for their production such as fungi, bacteria, yeast, transgenic plants or animal cell lines.

Preferred xylanolytic enzymes of fungal origin are xylanases originally derived from a strain of Aspergillus, in particular *Aspergillus aculeatus, Aspergilius awamori, Aspergillus niger, Aspergillus tubigensis,* a strain of Cochliobolus, in particular *Cochliobolus carbonum,* a strain of Disporotrichum, in particular *Disporotrichum dimorphosporum,* a strain of Humicola, in particular *Humicola insolens,* a strain of Neocallimastix, in particular *Neocallimastix patriciarum,* a strain of Thermomyces, in particular *Thermomyces lanuginosus* (syn. *Humicola lanuginosa*), or a strain of Trichoderma, in particular *Trichoderma longibrachiatum* and *Trichoderma reesei.*

Preferred xylanolytic enzymes of bacterial origin are xylanases derived from a strain of Bacillus, in particular *Bacillus pumilus, Bacillus stearothermophilus,* a strain of Dictyoglomus, in particular *Dictyoglomus thermophilum,* a strain of Microtetraspora, in particular *Microtetraspora flexuosa,* a strain of Streptomyces, a strain of Thermotoga, in particular a strain of *Thermotoga neapolitana, Thermotoga maritima* and *Thermotoga thermarum,* or a strain of Rhodothermus.

In a preferred embodiment the animal feed additive of the invention comprises a xylanolytic enzyme of Type I derived from a strain of *Thermomyces lanuginosus* which is provided in the form of a monocomponent preparation.

In another preferred embodiment the animal feed additive of the invention comprises a xylanolytic enzyme of Type II derived from a strain of Trichoderma which is provided in the form of a monocomponent preparation.

Xylanolytic Activity

The xylanolytic activity can be expressed in FXU-units, determined at pH 6.0 with remazol-xylan (4-O-methyl-D-glucurono-D-xylan dyed with Remazol Brilliant Blue R, Fluka) as substrate.

A xylanase sample is incubated with the remazol-xylan substrate. The background of non-degraded dyed substrate is precipitated by ethanol as a stop reagent. The remaining blue color in the supernatant (as determined spectrophotometrically at 585 nm) is proportional to the xylanase activity, and the xylanase units are then determined relatively to an enzyme standard at standard reaction conditions, i.e. at 50.0° C. and 30 minutes reaction time in a 0.1 M phosphate buffer pH 6.0.

EXAMPLES

The invention is further illustrated with reference to the following examples which are not intended to be in any way limiting to the scope of the invention as claimed.

Example 1

Determination of Type of Zylanolytic Enzyme

This example demonstrates how xylanolytic enzymes can be distinguished by the way they affect the viscosity of a wheat suspension, and how they can be classified xylanolytic enzymes of Type I and Type II, respectively. Xylanolytic enzymes of Type I increase the initial viscosity of a wheat suspension, whereas the initial viscosity of a wheat suspension is unaffected or becomes decreased by the action of a xylanolytic enzyme of Type II.

Foregut digesta viscosity has been identified as a major nutritional constraint affecting digestibility of wheat and barley based broiler diets. A close correlation between the reduction of digesta viscosity results and improvements in chicken feed conversion efficiency have been found.

In this example six different xylanolytic enzymes are examined with respect to their activity on initial viscosity of a wheat suspension:

A) A multicomponent *Trichoderma reesei* (previously identified as *Trichoderma longibrachiatum*) xylanase preparation (enzyme complex, Novozym™ 431, available from Novo Nordisk A/S, Denmark);

B) A monocomponent *Aspergillus aculeatus* xylanase preparation obtained according to Example 3 of WO 94/21785;

C) A monocomponent *Humicola insolens* xylanase preparation obtained according to Example 1 of WO 92/17573;

D) A monocomponent *Thermomyces lanuginosus* xylanase preparation obtained according to Examples 1–3 of WO 96/23062;

E) A multicomponent *Humicola insolens* xylanase preparation (enzyme complex, Bio-Feed Plus CT, available from Novo Nordisk A/S, Denmark); and F) A multicomponent Trichoderma xylanase preparation (enzyme complex, Avizyme™ 1300, available from Finnfeeds, Finland).

The determination is carried out under conditions that mimic the conditions of the gastro-intestinal tract of poultries. Therefore two determinations are made, one after incubation for 45 minutes in presence of pepsin (the pepsin phase, which mimics the conditions of the gizzard), and one after additional 120 minutes in presence of pancreatin (the pancreatin phase, which mimics the conditions of the small intestine).

Therefore two samples and two reference solutions (blank sample, control) are prepared, each containing 8.00 g of ground wheat in 12 ml of a solution of 1.042 g of pepsin in 250 ml of 0.1 N HCl. After stirring for 2 minutes, a solution of the xylanase sample in question is added to the two samples, and this point is accorded the time zero (t=0). The controls are added the same volume of a 1M $NaHCO_3$.

After 45 minutes (t=45) of incubation under stirring at 40° C., 4 ml of a 1M $NaHCO_3$ solution is added to one of the samples, and this sample is now being cooled to 0° C. This sample represents the pepsin phase. Also at t=45, 4 ml 1M $NaHCO_3$ is added to one of the controls.

At the same time (t=45) 4 ml of the supernatant of a solution containing 200 mg pancreatin in 50 ml of 1M $NaHCO_3$ solution is added to the second sample. After additional 120 minutes (t=165) of incubation under stirring at 40° C. the sample is cooled to 0° C. This sample represents the pancreatin phase. Also at t=165, 4 ml 1M $NaHCO_3$ is added to the the second control.

After centrifugation, the supernatants of the two samples are subjected to viscosity determination on a Brookfield DV-III viscosimeter at 40° C., using spindle no. 18. The viscosity is determined relative to the viscosity of the blank sample.

Figure 2:
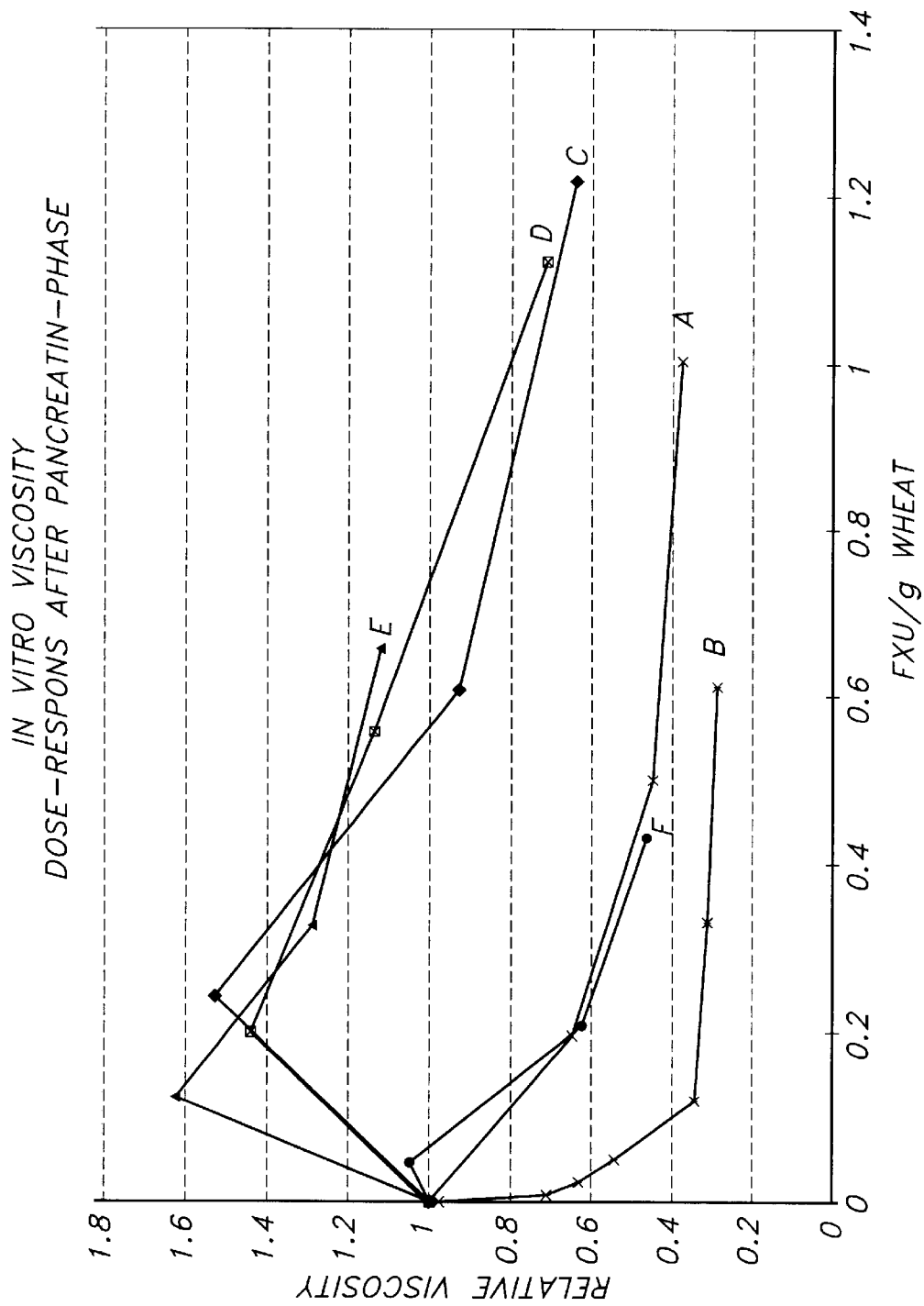
FIG. 2 shows the action of the same six enzymes as in FIG. 1 on the viscosity of a wheat suspension, also presented as relative viscosity (%) versus enzyme concentration (FXU/g wheat), but here determined after the so-called pancreatin phase according to Example 1.

The results of these determinations are presented as dose/response shown in the appended FIGS. 1–2. From these figures it is noticed that the xylanolytic enzymes designated above as C, D and E represent xylanolytic enzymes of Type I that increase the initial viscosity of the wheat suspension, and the xylanolytic enzymes designated above as A, B and F represent xylanolytic enzymes of Type II that decrease the initial viscosity of the wheat suspension.

Example 2

Effect of Mixtures of Xylanolytic Enzymes of Type I and Type II

This example demonstrates the effect of mixtures of xylanolytic enzymes of Type I and Type II on viscosity reduction of a wheat suspension.

Using the procedure described in example 1, above, combinations of the Type I enzymes C, D and E with the Type II xylanases A and B was examined.

The activity of the Type I xylanases was varied as shown in Table 1 (as in example 1), while the activity of the Type II xylanases was kept constant at the dose that gave 30% (preparations A and B) or 60% (preparation B) viscosity reduction after the pancreatin phase; i.e. for preparation B an activity of 0.01 FXU/g wheat, which resulted in a relative viscosity of 0.7, and an activity of 0.12 FXU/g, which resulted in a relative viscosity of 0.4; and for preparation A an activity of 0.20 FXU/g wheat, which resulted in a relative viscosity of approximately 0.7 (FIG. 2).

Table 1 shows the relative viscosity of the in vitro test system after addition of different xylanase combinations and also the single Type I enzymes. The viscosity is relative to the viscosity of a parallel incubation without added enzyme.

Using only a xylanase of type I, rather high doses have to be applied with a view to reducing the viscosity. However, when admixing with a xylanase of type II, a reduced viscosity results even in those cases in which the overall concentration of xylanase I+ xylanase II is smaller than that concentration of xylanase I alone, which had to be applied for observing any effect on the viscosity. When mixing for instance 0.12 FXU of xylanase B with 0.25 FXU of xylanase C (i.e. overall activity 0.37 FXU) a viscosity reduction of approximately 50% is obtained in the pepsin phase—as compared with a much smaller viscosity reduction of 11% when as much as 1.2 FXU of xylanase C is used, without admixed type II xylanase. Usually the enzyme costs are set on an activity basis, and accordingly, when using a mixture of the type I and the type II enzymes, the enzyme costs can be reduced.

Moreover, the effect on viscosity of a wheat suspension of two individual Type I and Type II xylanase preparations (preparations D and A, respectively) has been compared to that of the mixture of these two preparation as well as a theoretically calculated additive effect. For preparation D three activity levels were chosen, and for preparation A one activity level (that which resulted in a 30% viscosity reduction, i.e. a relative viscosity of 0.7) was chosen. The results of these experiments are presented in FIGS. 3 and 4.

Figure 3:
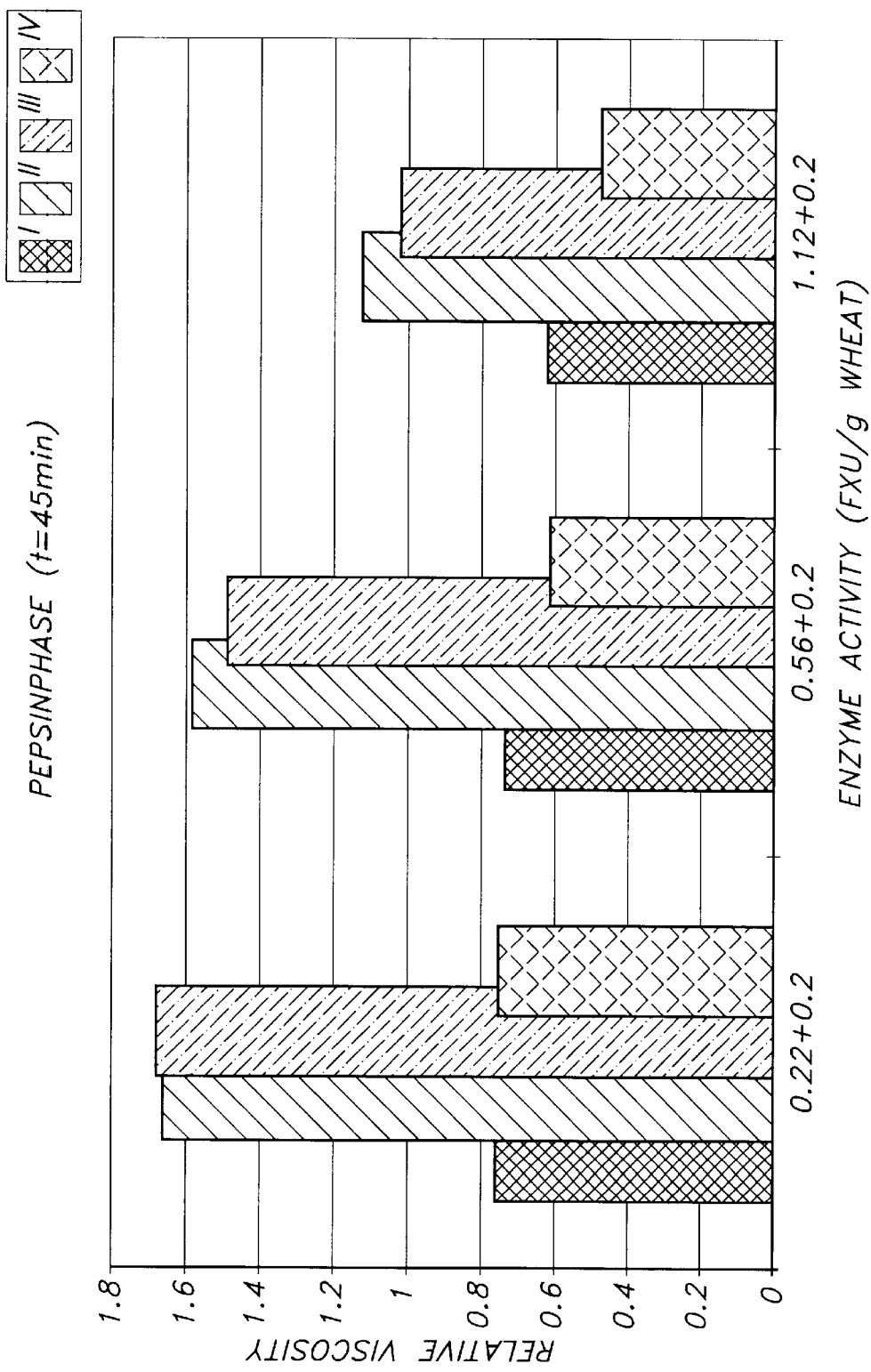
FIG. 3 shows the effect, determined after the pepsin phase, on the viscosity of a wheat suspension of two individual Type I and Type II xylanase preparations (viz. preparations D and A, respectively) compared to that of the mixture of these two preparations as well as a theoretically calculated additive effect; the effect is presented as % relative viscosity; columns I the combined effect of preparations A and D; columns II theoretical additive effect of preparations A and D; columns III the effect of preparation D alone; and columns IV the effect of preparation A alone.
Figure 4:
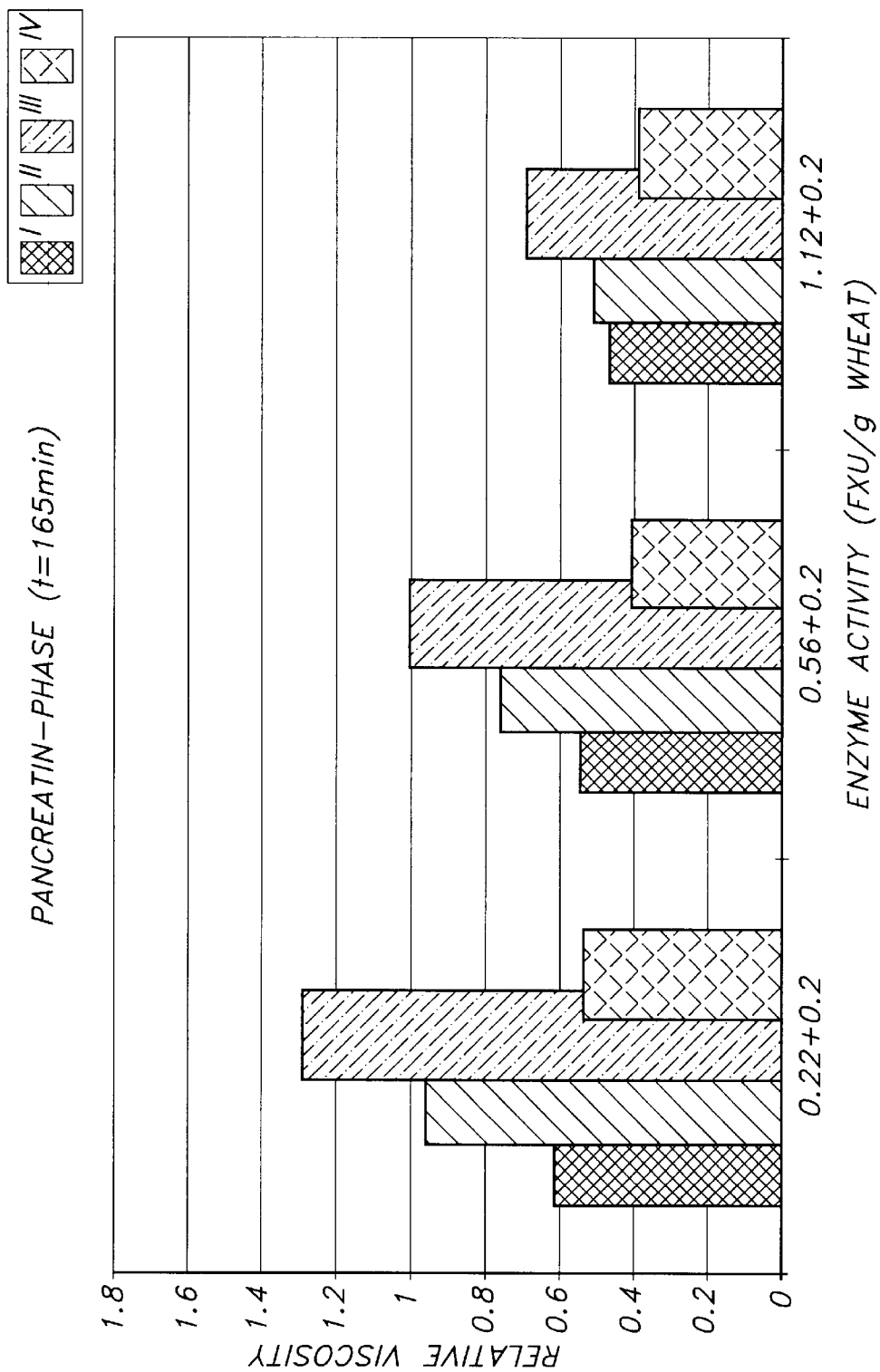
FIG. 4 shows, as in FIG. 3, the effect on the viscosity of a wheat suspension of the same two individual Type I and Type II xylanase preparations, but here as determined after the pancreatin phase.

FIG. 3 shows the effect after the pepsin phase (after incubation for 45 minutes, cf. Example 1), and FIG. 4 shows the effect after the pancreatin phase (after incubation for 165 minutes, cf. Example 1). In these figures, the effect is presented as % relative viscosity.

The first columns (I) of each cluster represent the actual relative viscosity determined using a mixture of preparations D and A. Thus, in the first cluster of FIGS. 3 and 4, columns (I), a mixture of 0.22 FXU/g wheat of preparation D and 0.2 FXU/g wheat of preparation A was used, in the second cluster, a mixture of 0.56 FXU/g wheat of preparation D and 0.2 FXU/g wheat of preparation A was used, and in the third cluster, a mixture of 1.12 FXU/g wheat of preparation D and 0.2 FXU/g wheat of preparation A was used.

The second columns (II) of each cluster of each of FIG. 3 and FIG. 4 represent the theoretical viscosity of the mixture, calculated using a multiplicative statistical model. Thus, referring for example to FIG. 3, column (II) of the first cluster represents the theoretically additive effect of using 0.22 FXU/g wheat of preparation D and 0.2 FXU/g wheat of preparation A, column (II) of the second cluster represents the theoretically additive effect of using 0.56 FXU/g wheat of preparation D and 0.2 FXU/g wheat of preparation A, and column (II) of the third cluster represents the theoretically additive effect of using 1.12 FXU/g wheat of preparation D and 0.2 FXU/g wheat of preparation A.

The third and fourth columns (III and IV) of each cluster represent the actual relative viscosity determined using each of preparations D and A alone, respectively. Thus, e.g. in the first cluster of FIG. 3, columns III and IV represent the effect of using 0.42 FXU/g wheat of preparation D and 0.42 FXU/g wheat of preparation A, respectively.

It is apparent from these figures, that the actual viscosity determined using a mixture of preparations A and D is lower than the calculated additive value, and this is owing to a synergy between the enzymes.

It is presently contemplated that xylanases of Type I, such as preparation D, are acting preferably or initially (at low doses) on insoluble xylans (constituting approximately

TABLE 1

Relative Viscosity of Wheat Suspensions

| Type II \ | Type I | | Xylanase C | | | | Xylanase D | | | Xylanase E | | |
| --- | --- | --- | --- | --- | --- | --- | --- | --- | --- | --- | --- | --- |
| FXU/g | wheat | 0.25 | 0.3 | 0.6 | 1.2 | 0.22 | 0.56 | 1.12 | 0.1 | 0.3 | 0.7 |
| No mix. | Pepsin | 179 | 170 | 121 | 89 | 180 | 161 | 122 | 123 | 178 | 139 |
|  | Pancreatin | 150 | 146 | 118 | 62 | 140 | 117 | 79 | 158 | 139 | 109 |
| +Xyl B | Pepsin |  | 118 | 106 | 84 | 97 | 95 | 83 |  |  |  |
| 0.01 | Pancreatin |  | 99 | 82 | 70 | 76 | 70 | 58 |  |  |  |
| +Xyl B | Pepsin | 49 |  | 52 | 54 | 97 | 95 | 83 | 49 | 51 | 54 |
| 0.12 | Pancreatin | 36 |  | 39 | 34 | 76 | 70 | 58 | 38 | 40 | 40 |
| +Xyl A | Pepsin | 87 |  | 77 | 77 | 77 | 74 | 64 | 49 | 52 | 54 |
| 0.2 | Pancreatin | 62 |  | 55 | 50 | 62 | 55 | 48 | 36 | 39 | 34 |

80–90% of the total amount of xylans), thus liberating pentosans which are soluble, and therefore the viscosity is increased. These pentosans, however, are preferred substrates for the Type II xylanases, such as preparation A, so when acting in combination xylanases I and II degrade more xylans and the viscosity is adequately reduced. Still further, also other nutrients, which were originally embedded by the xylans, are made nutritionally available.

In general the synergistic effect is most pronounced when the total activity is low. This is probably because at higher activities of Type I xylanases, they will also start degrading the soluble pentosans, thus reducing the synergistic effect.

In addition, statistical analysis showed that the synergistic effect is highest during the pepsin phase, probably because the viscosity reduction here is smaller than in the pancreatin phase, thus leaving more room for improvement.

What is claimed is:

1. An animal feed additive which comprises (i) at least one xylanolytic enzyme that increases the initial viscosity of a wheat suspension (Type I enzyme) and (ii) at least one xylanolytic enzyme that decreases or leaves unaffected the initial viscosity of a wheat suspension (Type II enzyme), wherein said Type I and said Type II enzymes are mixed at an activity ratio of between about 2/8 and about 8/2.

2. The animal feed additive according to claim 1, wherein said ratio is between about 3/7 and about 7/3.

3. The animal feed additive according to claim 2, wherein said ratio is between about 4/6 and about 6/4.

4. The animal feed additive according to claim 3, wherein said ratio is about 1/1.

5. An animal feed additive according to claim 1, further comprising at least one carrier or excipient.

6. The animal feed additive according to claim 1, wherein said Type I enzyme is derived from a strain of *Humicola insolens*.

7. The animal feed additive according to claim 1, wherein said Type I enzyme is derived from a strain of *Thermomyces lanuginosus*.

8. The animal feed additive according to claim 1, wherein said Type II enzyme is derived from a strain of *Aspergillus aculeatus*.

9. The animal feed additive according to claim 1, wherein said Type II enzyme is derived from a strain of Trichoderma.

10. The animal feed additive according to claim 9, wherein said *Trichoderma* strain is selected from the group consisting of *Trichoderma longibrachiatum* and *Trichoderma reesei*.

11. The animal feed additive according to claim 1, wherein at least one of said xylanolytic enzymes is a monocomponent preparation.

12. The animal feed additive according to claim 7, wherein said Type I enzyme is a monocomponent preparation.

13. The animal feed additive according to claim 9, wherein said Type II enzyme is a monocomponent preparation.

14. The animal feed additive according to claim 11, wherein all of said xylanolytic enzymes are monocomponent preparations.

15. The animal feed additive according to claim 11, further comprising one or more additional feed enhancing enzymes.

16. The animal feed additive according to claim 15, wherein the additional feed enhancing enzymes are selected from the group consisting of other xylanases; α-galactosidases; β-galactosidases; phytases; β-glucanases; xylosidases; galactanases; endoglucanases; pectin degrading enzymes selected from the group consisting of pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases; mannanases; β-mannosidases; mannan acetyl esterases; xylan acetyl esterases; proteases; and lipolytic enzymes.

17. A method of preparing an animal feed additive according to claim 1, said method comprising mixing:
    (i) one or more Type I xylanolytic enzymes; and
    (ii) one or more Type II xylanolytic enzymes.

18. A method according to claim 17, further comprising mixing said Type I and Type II enzymes with at least one carrier or excipient.

19. A method for reducing the viscosity of animal feed, said method comprising adding to said feed
    (i) at least one xylanolytic enzyme that increases the initial viscosity of a wheat suspension (Type I enzyme); and
    (ii) at least one xylanolytic enzyme that decreases or leaves unaffected the initial viscosity of a wheat suspension (Type II enzyme), wherein said Type I and said Type II enzymes are added to said feed at an activity ratio of between about 2/8 and about 8/2.

20. A method for preparing an animal feed, said method comprising adding to said feed
    (i) at least one xylanolytic enzyme that increases the initial viscosity of a wheat suspension (Type I enzyme); and
    (ii) at least one xylanolytic enzyme that decreases or leaves unaffected the initial viscosity of a wheat suspension (Type II enzyme)), wherein said Type I and said Type II enzymes are added to said feed at an activity ratio of between about 2/8 and about 8/2.

21. An animal feed additive which comprises (i) at least one xylanolytic enzyme that increases the initial viscosity of a wheat suspension (Type I enzyme) and (ii) at least one xylanolytic enzyme that decreases or leaves unaffected the initial viscosity of a wheat suspension (Type II enzyme), wherein said Type I enzyme is derived from a strain of *Thermomyces lanuginosus*.

22. An animal feed additive which comprises (i) at least one xylanolytic enzyme that increases the initial viscosity of a wheat suspension (Type I enzyme) and (ii) at least one xylanolytic enzyme that decreases or leaves unaffected the initial viscosity of a wheat suspension (Type II enzyme), wherein said Type II enzyme is derived from a strain of *Aspergillus aculeatus* or a strain of Trichoderma.

23. An animal feed additive which comprises (i) at least one xylanolytic enzyme that increases the initial viscosity of a wheat suspension (Type I enzyme); (ii) at least one xylanolytic enzyme that decreases or leaves unaffected the initial viscosity of a wheat suspension (Type II enzyme), and (iii) one or more additional feed enhancing enzymes.

24. The animal feed additive according to claim 17, wherein the additional feed enhancing enzymes are selected from the group consisting of other xylanases; α-galactosidases; β-galactosidases; phytases; β-glucanases; xylosidases; galactanases; endoglucanases; pectin degrading enzymes selected from the group consisting of pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases; mannanases; β-mannosidases; mannan acetyl esterases; xylan acetyl esterases; proteases; and lipolytic enzymes.

* * * * *